(12) United States Patent
Graham et al.

(10) Patent No.: US 11,421,313 B2
(45) Date of Patent: Aug. 23, 2022

(54) ARTICLE AND A METHOD OF MAKING AN ARTICLE

(75) Inventors: Terence Graham, Oxfordshire (GB); Andrew Robert McCabe, Oxfordshire (GB); Thomas Campbell Prentice, Oxfordshire (GB)

(73) Assignee: ZIRCOTECIP LIMITED, Abingdon (GB)

( * ) Notice: Subject to any disclaimer, the term of this patent is extended or adjusted under 35 U.S.C. 154(b) by 30 days.

(21) Appl. No.: 12/988,834

(22) PCT Filed: Apr. 21, 2009

(86) PCT No.: PCT/EP2009/054762
§ 371 (c)(1),
(2), (4) Date: Oct. 21, 2010

(87) PCT Pub. No.: WO2009/130229
PCT Pub. Date: Oct. 29, 2009

(65) Prior Publication Data
US 2011/0039086 A1    Feb. 17, 2011

(30) Foreign Application Priority Data
Apr. 21, 2008   (GB) .................................... 0807261

(51) Int. Cl.
| | |
|---|---|
| *B32B 18/00* | (2006.01) |
| *C23C 4/10* | (2016.01) |
| *C23C 4/08* | (2016.01) |
| *A61L 27/32* | (2006.01) |
| *B60B 5/00* | (2006.01) |
| *A61L 27/04* | (2006.01) |
| *A61L 27/30* | (2006.01) |
| *A61L 27/42* | (2006.01) |

(Continued)

(52) U.S. Cl.
CPC ................ *C23C 4/08* (2013.01); *A61L 27/04* (2013.01); *A61L 27/30* (2013.01); *A61L 27/306* (2013.01); *A61L 27/32* (2013.01); *A61L 27/422* (2013.01); *B60B 5/00* (2013.01); *C23C 4/11* (2016.01); *C23C 28/321* (2013.01); *C23C 28/322* (2013.01); *C23C 28/345* (2013.01); *C23C 28/347* (2013.01); *C23C 28/3455* (2013.01);
(Continued)

(58) Field of Classification Search
CPC .................................. B32B 18/00; C23C 4/10
USPC ........................................... 428/220; 427/453
See application file for complete search history.

(56) References Cited

U.S. PATENT DOCUMENTS

| | | |
|---|---|---|
| 3,775,208 A | 11/1973 | Grigoleit et al. |
| 3,892,883 A | 7/1975 | Leclercq |

(Continued)

FOREIGN PATENT DOCUMENTS

| | | |
|---|---|---|
| CA | 2635713 A1 * | 11/2007 |
| CN | 101016614 A | 8/2007 |

(Continued)

OTHER PUBLICATIONS

Machine_English_translation_JP_06093406_A; Nishimura; Flame-Retardant Material; May 4, 1994; whole document (Year: 1994).*

(Continued)

*Primary Examiner* — Tahseen Khan
(74) *Attorney, Agent, or Firm* — Paul J. Roman, Jr., Esq.; Johnson, Marcou, Isaacs & Nix, LLC

(57) ABSTRACT

An article, at least a surface of the article being made of or containing an organic material, and a thermally sprayed layer of coating material on the surface.

49 Claims, 5 Drawing Sheets

(51) Int. Cl.
*C23C 28/00* (2006.01)
*C23C 4/11* (2016.01)

(52) U.S. Cl.
CPC ..... *A63B 2209/00* (2013.01); *A63B 2209/023* (2013.01); *Y02T 50/60* (2013.01)

(56) References Cited

U.S. PATENT DOCUMENTS

| | | | |
|---|---|---|---|
| 4,022,585 A | | 5/1977 | Kaye |
| 4,388,373 A | | 6/1983 | Longo et al. |
| 4,704,328 A | | 11/1987 | Imao et al. |
| 4,997,704 A | | 3/1991 | Jarrabet |
| 5,056,630 A | * | 10/1991 | Fujii et al. ................ 188/24.13 |
| 5,236,773 A | | 8/1993 | Sorathia et al. |
| 6,258,218 B1 | | 7/2001 | Burton |
| 2001/0003336 A1 | * | 6/2001 | Abbott .................... F27D 11/02 219/543 |
| 2002/0059727 A1 | | 5/2002 | Graf et al. |
| 2005/0129972 A1 | * | 6/2005 | Matsumoto ........... C23C 28/321 428/632 |
| 2008/0254227 A1 | * | 10/2008 | Stoltenhoff et al. .......... 427/447 |

FOREIGN PATENT DOCUMENTS

| | | |
|---|---|---|
| DE | 4116639 | 11/1992 |
| EP | 0514640 | 11/1992 |
| GB | 1278714 | 6/1972 |
| GB | 1397955 | 6/1975 |
| JP | 06093406 A * | 4/1994 |
| WO | WO 01/46324 | 6/2001 |
| WO | 02/04694 A1 | 1/2002 |

OTHER PUBLICATIONS

Alarifi m. ibrahim; Investigation the conductivity of carbon fiber composites focusing on measurement techniques under dynamic and static loads; Aug. 26, 2019; journal of materials research and technology; whole document (Year: 2019).*

Liu et al. "Influence of bond coat on shear adhesion strength of erosion and thermal resistant coating . . . " Surf. & Coat. Tech., 2006, pp. 2696-2700, v. 201, Elsevier.

International Searching Authority (ISA), International Search Report and Written Opinion of the ISA, PCT/EP2009/054762, dated Dec. 2, 2009.

Guo, et al., "Protection of Polymer matrix composite material with ceramic coatings," Transactions of the China Welding Institution Nov. 2005 (no date), all enclosed pages cited.

Chambers, et al., "Sputtering on Polymeric Composites," Surface and Coatings Technology, 41 (1990), all enclosed pages cited.

Taylor, et al., "Comparison of stress and structural composition of sputter deposited thick coatings of TiB2 + Ni on polymeric composites," J. Vac. Sci. Technol. A 10(4), Jul./Aug. 1992, all enclosed pages cited.

Ashari, et al., "Thermal Spray Coatings for Fiber Reinforced Polymer Composites," Proceedings of the 15th International Thermal Spray Conference, May 25-29, 1998, all enclosed pages cited.

Thermal Spray Flexicord Technical Bulletin, Issued Oct. 2000, all enclosed pages cited.

Miyoshi, et al., "Erosion of bare and coated polymer matrix composites by solid particle impingement," 28th International Conference on Advanced Ceramics and Composites (2004), all enclosed pages cited.

Davis, J.R., "Handbook of Thermal Spray Technology," (2005) all enclosed pages cited.

Zhang, et al., "Depositing light ceramic coating on high temperature polymer matrix composite substrate," Transactions of the China Welding Institution Mar. 2005, (2006) all enclosed pages cited.

Liu, et al., "Arc Sprayed erosion-resistant coating for carbon fiber reinforced polymer matrix composite substrates," Surface & Coatings Technology 200 (2006), all enclosed pages cited.

Beauvais, et al., "Plasma Sprayed Biocompatible Coating on PEEK Implants," Thermal Spray 2007, all enclosed pages cited.

Oerlikon Metco Material Product Data Sheet: "Magnesia-Stablized Zirconium Oxide Thermal Spray Powers," (2014), all enclosed pages cited.

* cited by examiner

ARTICLE AND A METHOD OF MAKING AN ARTICLE

The present application is related to, and is a U.S. National Stage § 371 Application of, PCT/EP2009/054762, filed Apr. 21, 2009, which is related to, and claims the priority benefit of, Great Britain Patent Application Serial No. 0807261.3, filed Apr. 21, 2008. The contents of each of these applications are hereby incorporated by reference in their entirety into this disclosure.

The invention relates to an article and a method of making an article.

It is known to coat metal parts, for example engine parts, by plasma spraying with a layer of ceramic or metal material. In plasma spraying, the material to be deposited is melted and propelled towards the substrate to be coated. The plasma jet temperature may be of the order of 20,000 K.

According to one aspect of the invention, there is provided an article, the article including a substrate, at least a surface of the substrate being made of or containing an organic material, and a thermal sprayed first layer of coating material on the surface, and a further layer on the first layer the coating material of the first layer being wholly or principally metal material, the first layer being less than 200 micrometres in thickness and the further layer being of a material with a higher melting point than the coating material of the first layer.

The high temperature associated with thermal spraying has previously been considered to prohibit its use for the surface treatment of organic material, but the inventors have found that it is possible and provides a good result. In this way, a high melting point material can be provided as a layer on a surface made of or containing inorganic material in a manner which would not previously have been possible without deleterious melting or degassing of the inorganic material.

The surface of the article may be made of any suitable organic material and may be made of plastics material or a composite material including a matrix made of a plastics material. The surface may be made of glass fibre reinforced plastic composite material or the like, and in a preferred embodiment the surface is made of carbon fibre composite material. Carbon fibre composite materials are popular in a range of industries primarily because of their high strength and low weight.

Preferably the coating material of the first layer has a melting temperature of no more than 1200° C., more preferably under 700° C. The layer of coating material is preferably a metal material, but in another embodiment it may be a zirconate ceramic material. Where the coating material is a metal material it may include one or more of tin, copper, aluminium, silver, gold, lead and zinc. In preferred embodiments the coating material is copper or aluminium or a copper aluminium alloy.

The coating material is preferably sprayed at a rate of less than 100 g/min, more preferably less than 70 g/min, and most preferably less than 40 g/min. A low deposition rate minimises heat transfer to the substrate, thus minimising risk of damage to the substrate.

The layer of coating material may be of any desired thickness and may for example be up to 150 micrometres in thickness, preferably up to 100 micrometres. The layer of coating material is preferably at least 2 micrometres thick.

The layer of coating material may cover the whole of the said surface of the article or may cover only a selected part of the surface. This may be to achieve a particular technical result, such as electrical conductivity, electromagnetic shielding or electromagnetic transmission or heat resistance, for example, in selected areas or may alternatively or in addition be for decorative purposes.

According to a further aspect of the present invention, there is provided an article, the article including a substrate, the substrate being made of or containing an organic material, the article further including a first layer of coating material intermediate between the substrate and a further layer, the first layer being incorporated in the organic material of the substrate.

The layer of coating material may comprise a powder. Preferably the layer of coating material is a foil.

The further layer may also be a thermally sprayed layer. The further layer may be made of any suitable material and may be made of a material with a higher melting point than the coating material. In this way, a high melting point material can be provided as a layer on a surface of or containing inorganic material in a manner which would not previously have been possible without deleterious melting or degassing or other heat damage to the organic material. In preferred embodiments the further layer is made wholly or principally of ceramic or metal or ceramic and metal, more preferably wholly or principally of ceramic material. Where the further layer is made of metal, the further layer may be designed to achieve desired electrical or electromagnetic properties. Where the further layer is made from ceramic, the further layer may be designed to achieve desired thermal barrier or mechanical damage resistance properties. Where the further layer is ceramic, it may comprise at least 50% of at least one of zirconia, titania, or alumina.

According to another aspect of the present invention, there is provided an article, the article including a substrate, at least a surface of the substrate being made of or containing an organic material, and a thermal sprayed first layer of coating material on the surface, and a further layer on the first layer, the coating material of the first layer being wholly or principally metal material, the further layer comprising at least 50 wt-% zirconia, titania or alumina.

The further layer preferably comprises wholly or principally at least one of zirconia, titania, or alumina. The further layer may also include at least one of yttria and magnesia.

Preferably, the level of porosity in the further layer is preferably greater than 5%, and more preferably greater than 15%. This allows a low deposition rate to be used and also allows the further layer to better accommodate strain associated with thermal mismatch. Therefore, the coating layer need not be as thick in order to protect the substrate from heat damage during deposition of the further layer or to take up the flex associated with thermal mismatch.

The further layer is preferably sprayed at a rate of less than 150 g/min, more preferably less than 100 g/min, and most preferably less than 50 g/min. A low deposition rate minimises heat transfer to the substrate, thus minimising risk of damage to the substrate. As heat transfer to the substrate is minimised, the coating layer thickness can also be minimised thus allowing a low weight article.

The article may include at least one additional layer on the further layer. The or each additional layer may also be a thermal sprayed layer or may be deposited in another suitable way such as by electroless deposition, physical vapour deposition (PVD), chemical vapour deposition (CVD) or as a paint or by printing. The or at least one additional layer or each additional layer may be principally or wholly made of ceramic or metal or ceramic and metal. Such layers may provide heat or light reflectivity, abrasion resistance, chemical resistance, impact resistance, electrical conductivity or radar signature modification.

The total thickness of the layers may be such as to provide increased local mechanical strength. The total thickness may be as high as several hundred micrometres.

The further layer may be at least as thick as the first layer, and preferably the further layer is thicker than the first layer. The further layer may be at least 100 micrometres thick, preferably at least 150 micrometres thick. The further layer is preferably not greater than 300 micrometres thick, more preferably not greater than 250 micrometres thick. The article may be a bicycle wheel and the layers are on the braking area of the rim of the wheel. The article may be a golf club and the layers are on at least one of the striking face and ground engaging face of the golf club.

The article may be a medical implant, preferably a bone or tooth implant. Where the article is a medical implant, the first layer may be wholly or principally of silver. The further layer may be wholly or principally of titanium. There may be an additional layer wholly or principally of hydroxyapatite.

According to a further aspect of the present invention, there is provided a bicycle wheel, the bicycle wheel including a rim for a bicycle tyre, the rim including an outer surface wholly or principally of carbon fibre composite material, the wheel including on the outer surface of the rim a first layer of coating material and a further layer, the further layer being wholly or principally of ceramic or metal or ceramic and metal and forming a braking surface to be contacted by a brake block.

The further layer may be a layer wholly or principally of ceramic, and preferably is at least 50% titanium dioxide. The first layer may be a thermal sprayed layer wholly or principally of metal. The further layer may be a thermal sprayed layer of material with a higher melting point than the melting point of the material of the first layer. The bicycle wheel is preferably wholly or principally of carbon fibre composite material.

According to another aspect of the present invention, there is provided a golf club, the head of the golf club being wholly or principally of carbon fibre composite material, at least one of the striking face and the ground engaging face of the golf club including thereon a first layer of coating material and a further layer, the further layer being wholly or principally molybdenum or tungsten.

According to a further aspect of the present invention, there is provided a bone or tooth implant comprising a substrate, the substrate being wholly or principally made of carbon fibre composite material, a surface of the substrate which is arranged to engage bone or tooth when implanted having a thermal sprayed first layer of coating material, and a thermal sprayed top layer of hydroxyapatite.

According to another aspect of the invention there is provided a method of coating a substrate surface made of or containing an organic material, the method comprising thermal spraying the surface with a first layer of coating material to a thickness of less than 200 micrometres and depositing a further layer on the first layer, the coating material of the first layer being wholly or principally metal material, the further layer being of a material with a higher melting point than the coating material of the first layer.

Any suitable thermal spraying technique may be used, such as wire spraying, and in a preferred embodiment, the layer of coating material is plasma sprayed onto the surface. Any suitable gas may be used for the plasma spraying and in a preferred embodiment the gas is nitrogen.

The method may include chemical modification of the surface prior to thermal spraying to promote adhesion or reduce substrate outgassing. The method may include temperature treatment of the surface prior to thermal spraying to reduce substrate outgassing. The method may include roughening the substrate surface prior to thermal spraying thereon. The roughening may be effected by mechanical abrasion, for example by grit blasting, or alternatively by chemical means, for example by etching.

The substrate surface may be made of any suitable organic material and may be made of plastics material or a composite material including a matrix made of a plastics material. The surface may be made of a composite such as glass fibre reinforced plastic composite material and in a preferred embodiment the surface is made of carbon fibre composite material. Carbon fibre composite materials are popular in a range of industries primarily because of their high strength and low weight.

The layer of coating material may be of higher melting point than the organic material. The layer of coating material is preferably a metal material, but in another embodiment it may be a zirconate ceramic material. Where the coating material is a metal material it may include one or more of tin, copper, aluminium, silver, gold, lead and zinc. In preferred embodiments the coating material is copper or aluminium or a copper aluminium alloy.

The first layer may be sprayed to at least 2 micrometres in thickness.

The layer of coating material may be applied to any desired thickness and may for example be from 2 to 200 micrometres in thickness, preferably from 2 to 150 micrometres in thickness, and most preferably from 2 to 100 micrometres in thickness.

The layer of coating material may be sprayed to cover the whole of the said surface of the substrate or may cover only a selected part of the surface. This may be to achieve a particular technical result, such as electrical conductivity, or heat resistance, for example, in selected areas or may alternatively or in addition be for decorative purposes.

The method may include depositing a further layer on the coating material.

According to a yet further aspect of the present invention, there is provided a method of coating a substrate surface made of or containing an organic material, the method comprising the steps of:

(1) depositing a first layer of coating material at the surface of the substrate so that the first layer is incorporated in the organic material of the substrate; and (2) depositing a further layer on the first layer.

Preferably, after the step of depositing the first layer there is step of removing any organic material on the first layer of coating material. The layer of coating material may comprise a foil. Alternatively, the layer of coating material may comprise powder particles. The resin outside the layer of coating material may be removed mechanically, for example by grit blasting, or electrochemically, for example using sodium hydroxide.

Alternatively, the layer of coating material may be a layer of foil and step (1) may comprise bonding the foil to the surface of the substrate.

The further layer may also be deposited by thermal spraying, such as plasma spraying. In preferred embodiments the further layer is made of ceramic or metal or ceramic and metal. Where the further layer is made of metal, the further layer may be designed to achieve desired electrical or electromagnetic properties. Where the further layer is made from ceramic, the further layer may be designed to achieve desired thermal barrier or mechanical damage resistance properties.

According to another aspect of the present invention, there is provided a method of coating a substrate surface made of or containing an organic material, the method comprising thermal spraying the surface with a first layer of coating material, the coating material of the first layer being wholly or principally metal material, and depositing a further layer on the first layer, the further layer comprising at least 50 wt-% of at least one of zirconia, titania, and alumina.

The further layer may comprise wholly or principally at least one of zirconia, titania, and alumina. The further layer may also include at least one of yttria and magnesia.

The method may include depositing at least one additional layer on the further layer. The or each additional layer may also be deposited by thermal spraying such as plasma spraying or may be deposited in another suitable way such as by electroless deposition, physical vapour deposition (PVD), chemical vapour deposition (CVD) or by painting, for example with specialist ceramic paint, or by printing, for example by screen printing. The or each additional layer may be made of any suitable material and may be made of ceramic or metal or ceramic and metal.

The total thickness of the deposited layers may be such as to provide increased local mechanical strength. The total thickness may be as high as several hundred micrometres, and in certain instances may be as much as several millimetres.

The further layer may be deposited to be at least as thick as the first layer, and preferably the further layer is deposited to be thicker than the first layer. The further layer may be deposited to be at least 100 micrometres thick, preferably at least 150 micrometres thick. The further layer may be deposited to be not greater than 300 micrometres thick, and preferably not greater than 250 micrometres thick.

The substrate may be a bicycle wheel and the layers are deposited on the area of the rim of the wheel which is frictionally clamped by brake blocks to brake the wheel.

The substrate may be the head of a golf club and the layers are deposited on at least one of the striking face and the ground engaging face of the golf club head.

The substrate may be a medical implant, preferably a bone or tooth implant. The first layer may be wholly or principally of silver. The further layer may be wholly or principally of titanium. There may be an additional layer wholly or principally of hydroxyapatite. The coating material may be sprayed at a rate of 100 g/min or less, preferably 70 g/min or less, and most preferably 40 g/min or less. The further layer may be sprayed at a rate of 150 g/min or less, preferably 100 g/min or less, most preferably 50 g/min or less.

According to another aspect of the present invention, there is provided a method of making a bicycle wheel, the bicycle wheel including a rim for a bicycle tyre, the rim including an outer surface wholly or principally of carbon fibre composite material, the method comprising depositing on the outer surface of the rim a first layer of coating material and a further layer, the further layer being wholly or principally of ceramic or metal or ceramic and metal and forming a braking surface to be contacted by a brake block.

Where the method is a method of making a bicycle wheel, the further layer may be a layer wholly or principally of ceramic, preferably at least 50% titanium dioxide. The first layer may be deposited by thermal spraying. The first layer may be wholly or principally of metal. The further layer may be deposited by thermal spraying. The further layer may be of a material with a higher melting point than the melting point of the material of the first layer. The bicycle wheel may be wholly or principally of carbon fibre composite material.

According to as further aspect of the present invention, there is provided a method of making a golf club, the head of the golf club being wholly or principally of carbon fibre composite material, the method comprising depositing on at least one of the striking face and the ground engaging face of the golf club a first layer of coating material and a further layer, the further layer being wholly or principally molybdenum or tungsten.

According to another aspect of the present invention, there is provided a method of making a bone or tooth implant comprising a substrate, the substrate being wholly or principally made of carbon fibre composite material, the method comprising thermal spraying a surface of the substrate which is arranged to engage bone or tooth when implanted with a first layer of coating material, and thermal spraying a top layer of hydroxyapatite.

Embodiments of the invention will now be described by way of example and with reference to the accompanying drawings, in which.

EMBODIMENT 1

Figure 1:
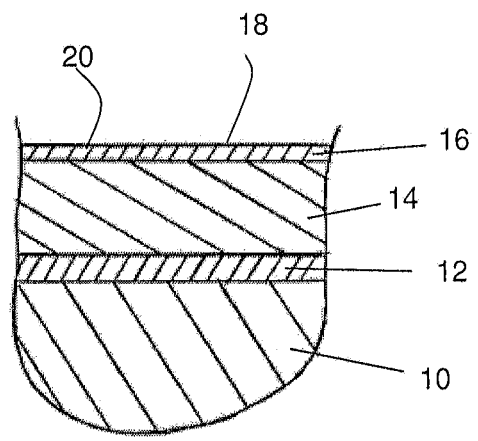
FIG. 1 is a side elevation in cross section of a coupon in a first embodiment of the invention.

A coupon 10 of carbon fibre reinforced plastics material of dimensions 150 mm×150 mm by 2 mm thick was carefully cleaned, using acetone, then wiped with tissue to remove any liquid. The clean coupon 10 was then grit blasted on one side using a siphon type grit blast system at 40 psi, with grit of between 0.4 and 0.6 mm size. The coupon 10 was blown with dry air to remove any debris and wiped with an acetone damp tissue.

The coupon 10 was then mounted onto a turntable in a plasma spray booth, containing a robot manipulation system. The spray system was set to work in nitrogen and aluminium powder feed set to spray at 30 gm/min. Nitrogen flow was preset to 50 litres/min. and current to 300 Amps. The robot was programmed to operate a ladder type spray pattern, at a stand off distance of 100 mm from the coupon, while the coupon 10 was rotated. In this way, an aluminium bond coat of approximately 25 μm thickness was applied. A second coat was then applied in the same way to provide a layer 12 with a total coating thickness of 50 μm.

Careful choice of the spray parameters ensures that the bond coat 12 "welds" itself to the surface of the coupon 10 with only micro-scale melting of the surface. It is key to control the amount of heat that is transferred via the metal spray to the coupon surface, thus minimising any localised damage to the carbon fibre reinforced plastics material.

Using the same type of spray program at 75 mm spray distance, using standard nitrogen plasma parameters, magnesium zirconate was plasma sprayed onto the aluminium coating on the coupon at 44 gm/min. Five coats gave a layer 14 with a thickness of 200 μm.

Repeating the aluminium spray program, but only applying one coat on top of the magnesium zirconate coating, gave a thin 25 μm metal layer 16. This was rubbed down using fine emery paper to give a smooth, shiny surface 18.

Carbon fibre reinforced plastics material is naturally relatively soft and susceptible to abrasion. The use of an aluminium bond layer 12 in this example allows a layer 14 of ceramic in the form of magnesium zirconate to be applied. This has good resistance to abrasion and other mechanical damage and is very hard. It is also resistant to corrosion or chemical attack and has very good thermal resistance forming a thermal barrier to protect the carbon fibre reinforced plastic material 10. It will be understood that it is the plastics matrix of the composite that is particularly vulnerable. Its protection by the ceramic layer 14 enables the use of carbon fibre composite material in environments which heretofore have been too harsh. The top layer of aluminium 16 gives an attractive finish to the visible surface 18, as well as providing further protection.

The resulting article 20 is very light in relation to its strength, certainly lighter than an equivalent in steel. An article 20 made in this way may be used for example as an automotive heat shield for extreme temperature conditions or as an aircraft tail cone.

If the aluminium layer 12 is connected to earth it provides electromagnetic shielding.

Instead of rubbing down the top layer 16 of aluminium with abrasive paper to achieve a smooth, shiny surface, the surface could be abraded for example by grit blasting or shot peening. Alternatively, the surface could be flamed to virtually melt, which results in a highly reflective surface finish.

EMBODIMENT 2

In this embodiment, a carbon fibre reinforced plastics part 30 is prepared for use as a heat shield. The intended environment requires higher temperature operation than normal for a carbon fibre reinforced plastics part. A carbon fibre reinforced plastics substrate 32 was pre-prepared in the same way as in embodiment 1, except that in this embodiment, the whole area of the surface of the substrate 32 is not being treated, only a selected area. Thus, areas 34 at the sides of the surface which do not require coating were masked with propriety masking tape to leave an unmasked central area.

In a plasma spray booth equipped for hand spraying, a copper bond coat 36 of 50 μm thickness was applied using an oxy-acetylene wire spray system, using the following parameters: oxygen=23 slpm, acetylene=18 slpm, feed rate of 25 g/min and a spray distance of 150 mm.

A further mask was then applied to side areas of the copper bond coat 36. A trained operator, using a hand held plasma torch, and parameters as follows: nitrogen=45 slpm, hydrogen=5 slpm, feed rate of 50 g/min, current=500 Amps, sprayed a layer 38 of magnesium zirconate onto the unmasked area of the bond coat 36, to give a creamy white ceramic layer 38 with a thickness of 300 μm.

Figure 2:
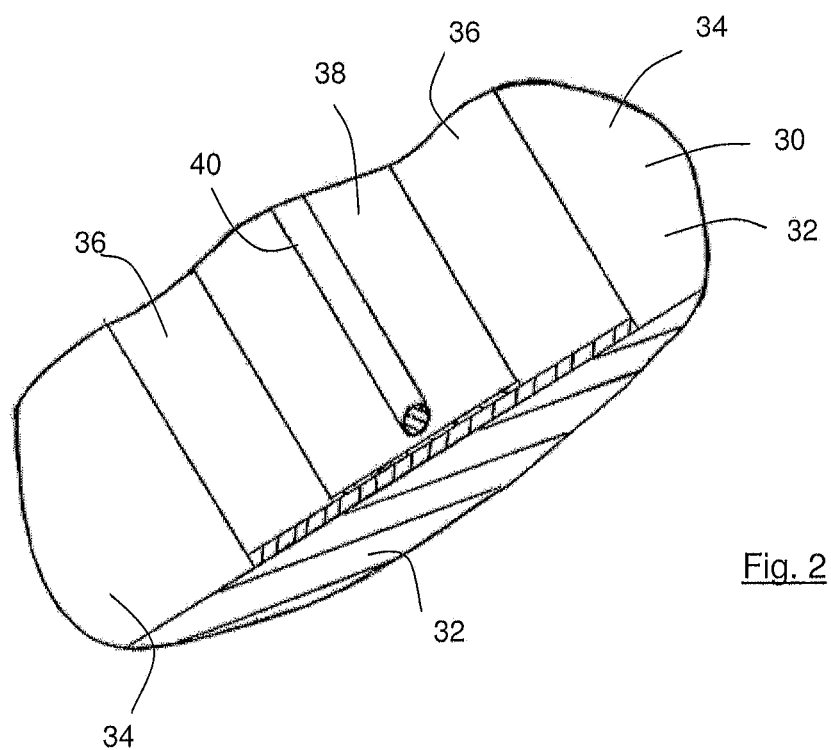
FIG. 2 is a fragmentary detail perspective view partly in cross section of a part in a second embodiment of the invention.

The part 30 is intended for use in an engine bay of a vehicle with an internal combustion engine. The part 30 will be situated near a hot rod 40 as shown in FIG. 2. The part is thus arranged so that the ceramic layer 38 is directly below the hot rod 40.

In use, as the rod 40 heats up, the ceramic layer 38 will act as a heat barrier to protect the carbon fibre reinforced plastics substrate 32. The copper layer 36, as well as acting as a bond layer to adhere the ceramic to the carbon fibre reinforced plastics substrate 32, also acts as a heat sink to conduct heat away and to dissipate heat. The uncoated parts 34 of the carbon fibre reinforced plastics substrate 32 are so far away from the rod 40 that the heat from the rod will not degrade them.

The fact that the layers are only applied where they are needed avoids unnecessary weight gain, which is important in a vehicle, as well as in other contexts.

The masking here is in strips and so is straightforward, but more complex masking can be used where required. In another embodiment, the masking may be used to enable a pattern or words to be sprayed onto a ceramic surface in a polishable metal for example to represent and display a trade mark. It is also possible to build up the surface coating by further metal spraying or by deposition in other ways to fabricate three dimensional features on the surface of the substrate. These might provide attachment or load bearing points or other features. In this case, the underlying metallic coat may be used to provide a degree of strengthening and load spreading. The use of an intermediate ceramic layer will protect the carbon composite material from conductive heat transfer via these features.

It is preferred to spray by robot, due to reproducibility, though where a component is of a complex shape, it may be more appropriate to use hand spraying.

EMBODIMENT 3

A carbon fibre reinforced plastics material part to form a car bonnet was carefully cleaned, using acetone, then wiped with tissue to remove any liquid. The clean part was then grit blasted on one side using a siphon type grit blast system at 40 psi, with grit of between 0.4 and 0.6 mm size. The part was blown with dry air to remove any debris.

The part was then mounted in a plasma spray booth, containing a robot manipulation system. The spray system was set to work in nitrogen and aluminium powder feed set to spray at 30 gm/min. Nitrogen flow was preset to 50 litres/min. and current to 300 Amps. The robot was programmed to operate a ladder type spray pattern, at a stand off distance of 100 mm from the part. In this way, an aluminium bond coat of approximately 25 μm thickness was applied. A second coat was then applied in the same way to provide a total coating thickness of 50 μm.

Gold was then deposited onto the part by wire-spray processing onto the aluminium coating on the part. A thickness of 150 μm was achieved. The surface was then chemically etched to achieve the desired finish.

The gold layer will conduct and dissipate heat. A gold foil lining tacked to the inside of an engine bay is known, but the layer of the present invention is firmly adhered to the carbon fibre composite part.

Although surface roughening has been described, some substrates may be sufficiently rough in their basic state not to require further roughening.

The invention provides a coating on a carbon fibre composite material which is very firmly adhered and by appropriate choice of top layers can provide a wide range of physical properties as desired.

EMBODIMENT 4

A carbon fibre reinforced plastic brake shield had a layer of aluminium foil bonded to the surface during the manufacturing process. Using appropriate protective clothing, the surface was treated with 3M NaOH solution and left for fifteen minutes. The surface was then water washed to remove any solution and debris and allowed to dry. The surface was roughened by grit blasting on one side using a siphon type grit blast system at 40 psi, with grit of between 0.4 and 0.6 mm size. The surface was then blown with dry air to remove any debris and wiped with an acetone damp tissue. Magnesium zirconate ceramic was then applied in the same manner as in Embodiment 2.

EMBODIMENT 5

A carbon fibre reinforced plastic heat shield, coated with magnesium zirconate ceramic, was subject to impact damage during routine maintenance.

A 50 μm layer of molybdenum was applied using a Metco™ 9 MB plasma spray gun, mounted on a Staubli™ robot, using the following parameters:
 Powder feed rate—25 g/min
 Nitrogen flow—80 scfh
 Hydrogen flow—10 scfh
 Current—500 A
 Spray distance—100 mm
 Traverse rate—150 mm/s The surface integrity of the ceramic was enhanced by the addition of this thin molybdenum coating, so that if any damage was done to the ceramic, the metal layer would held it together, preventing spalling.

An alternative application for this invention is applying coatings to polymeric materials and carbon fibre reinforced polymeric materials for medical and/or orthopaedic implants in cases where surface coatings (such as hydroxyapatite coatings) are required to promote bone in-growth and enhance the fixation of implants.

EMBODIMENT 6

Figure 3:
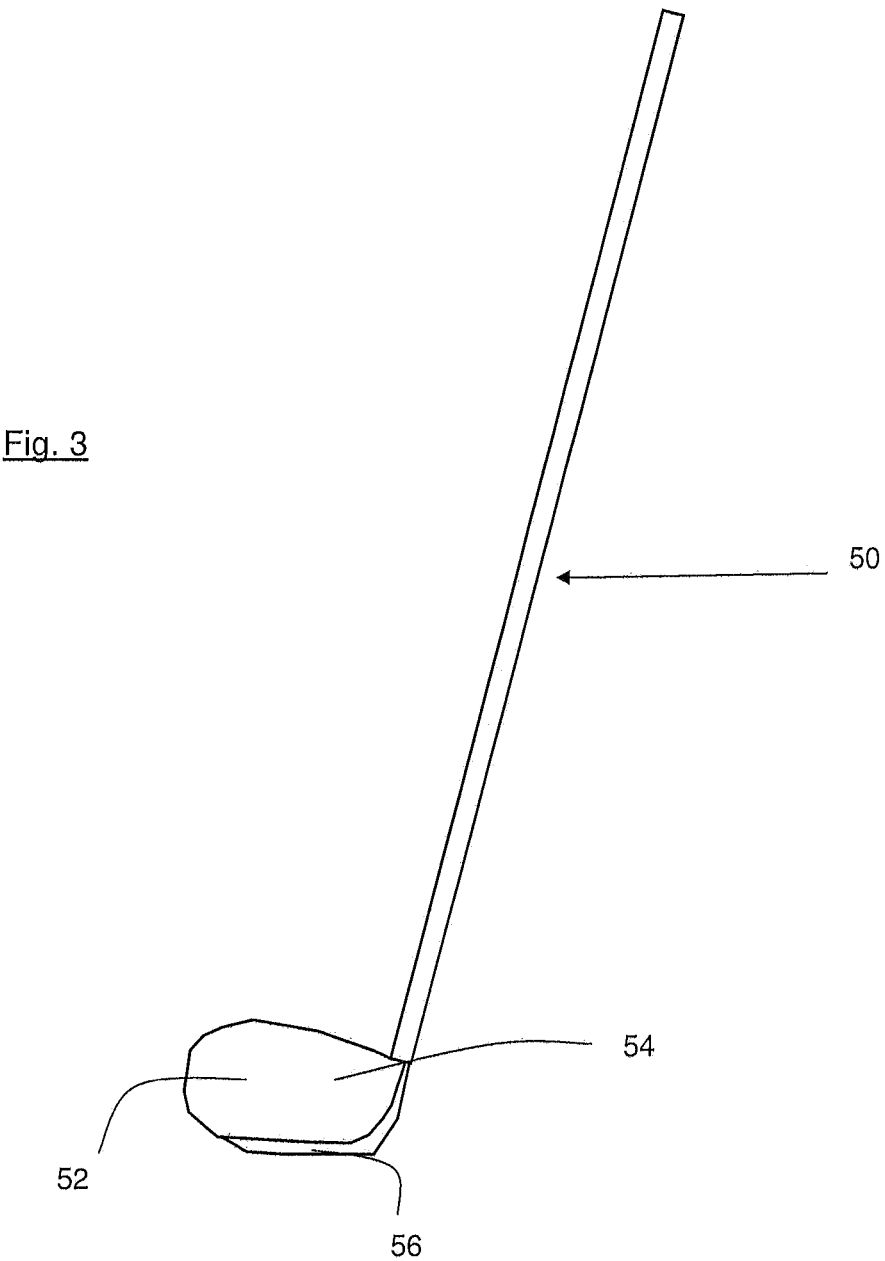
FIG. 3 shows a golf club according to Embodiment 6 of the present invention.
Figure 4:
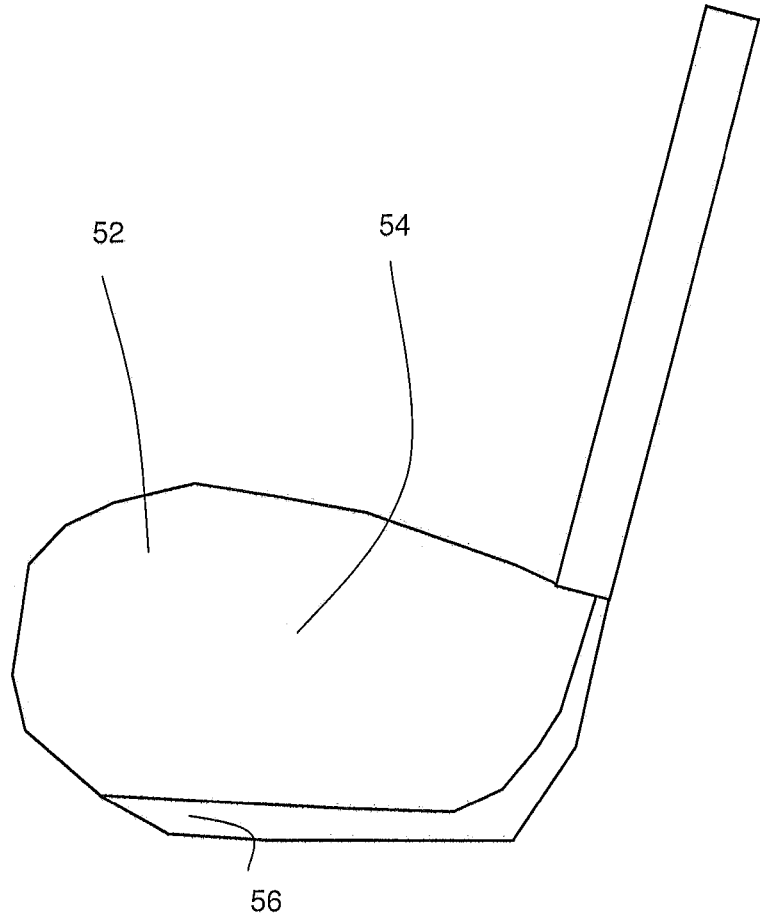
FIG. 4 shows the head of the golf club of FIG. 3, in fragmentary detail.

A golf club 50, as shown in FIGS. 3 and 4, with a carbon fibre reinforced plastic golf club head 52 was coated with magnesium zirconate ceramic on the striking face 54 of the head 52 and the bottom 56 of the head 52 in the same way as in Embodiment 2. To avoid impact damage, a 50 μm molybdenum layer was applied to the magnesium zirconate layer, in the same manner as described in Embodiment 5. As in Embodiment 5, if damage was done to the ceramic, the metal layer held it together, preventing spalling.

EMBODIMENT 7

Figure 5:
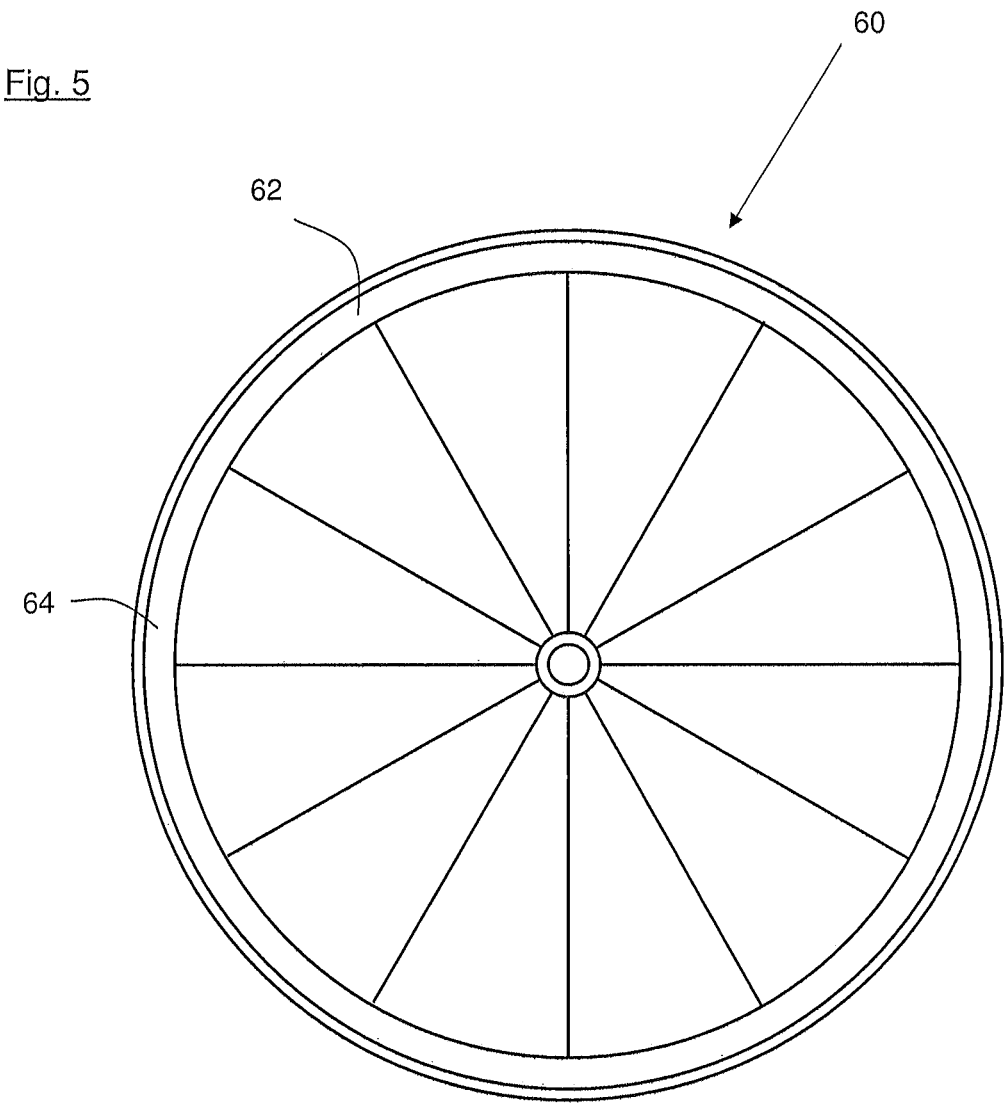
FIG. 5 shows a bicycle wheel according to Embodiment 7 of the present invention.

A carbon fibre reinforced plastic bicycle wheel 60, as shown in FIG. 5, quickly suffered wear when brakes pads were applied to the rim 62.

A bond coat comprising aluminium was plasma sprayed onto the braking area 64 of the rim 62 of the wheel 60, namely the area of the rim to be contacted by a brake block in use. The bond coat was deposited to a thickness of ~100 μm. The plasma spray parameters used were nitrogen 50 slpm, hydrogen 5 slpm, current 400 Amps, carrier gas 5 slpm, spray distance 100 mm, powder flow 45 g/min.

A 100 wt. % titanium dioxide ceramic layer was then applied on top of the bond coat by plasma spraying. The ceramic layer was applied to a thickness of ~200 μm. The plasma spray parameters used were Nitrogen 45 slpm, hydrogen 5 slpm, current 500 Amps, carrier gas 5 slpm, spray distance 75 mm, powder flow 65 g/min, ceramic powder particle size 50 to 90 micrometres.

The wear resistance of the wheel rim 62 was increased by the coatings.

EMBODIMENT 8

Figure 6:
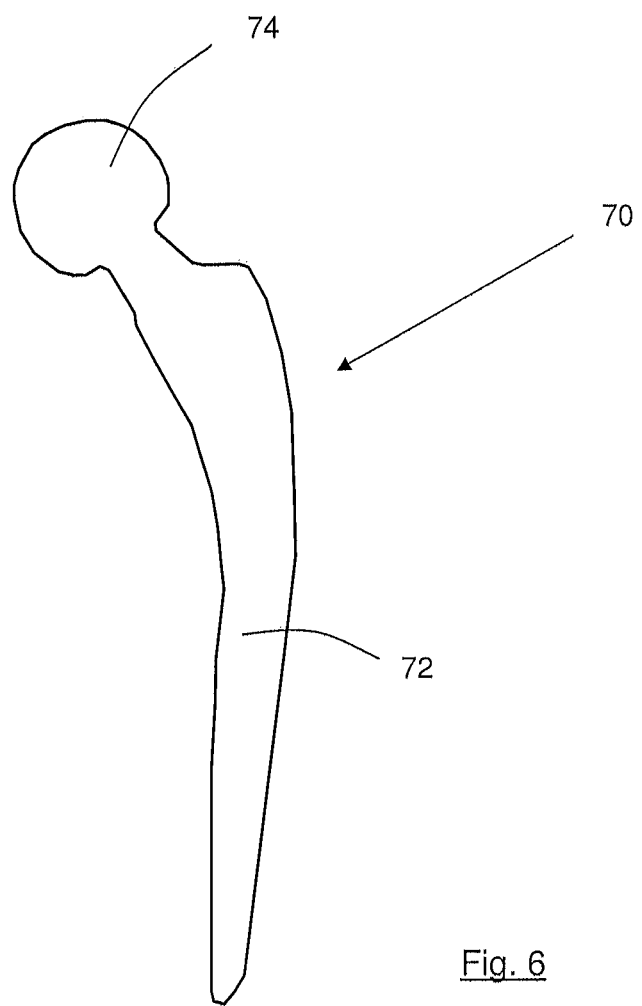
FIG. 6 shows a hip prosthesis according to Embodiment 8 of the present invention.

A carbon fibre reinforced plastic hip prosthesis 70, comprising a stem 72 and a ball 74, as shown in FIG. 6, was plasma sprayed with a 50 μm silver layer and then a 150 μm titanium layer. A 150 μm hydroxyapatite layer was then plasma sprayed onto the on the surface of the stem 72. The hydroxyapatite coating helped to promote bone ingrowth and enhance the fixation of the implant to the femur.

The invention claimed is:

1. An article, the article including a surface being made of a composite material including a matrix made of plastics material or a surface being made of an organic material, and a thermal sprayed first layer of coating material directly on the surface, and a further layer directly on the first layer, the coating material of the first layer being wholly metal material, the first layer being less than 200 micrometres in thickness and the further layer being of a material with a higher melting point than the coating material of the first layer and comprises at least 50 wt. % zirconia, titania or alumina, wherein the first layer is electrically conductive and may be connected to earth to provide electromagnetic shielding, and wherein the article is provided by a method in which the first layer is bonded to the surface with only micro-scale melting of the surface by thermally spraying at a rate of less than 70 g/min, and in which the further layer is bonded to the first layer with only micro-scale melting of the surface by thermally spraying particles of size 50 to 90 micrometres at a rate of less than 100 g/min.

2. An article according to claim 1, wherein the surface is made of carbon fibre composite material.

3. An article according to claim 1, wherein the first layer is up to 150 micrometres in thickness.

4. An article according to claim 1, wherein the first layer is up to 100 micrometres in thickness.

5. An article according to claim 1, wherein the further layer is a thermally sprayed layer, and has a level of porosity of greater than 15%.

6. An article according to claim 1, wherein the further layer is wholly or principally made of ceramic material.

7. An article according to claim 1, wherein the further layer comprises at least 50% of zirconia.

8. An article, the article including a surface being made of a composite material including a matrix made of plastics material or a surface being made of an organic material, and a thermal sprayed first layer of coating material directly on the surface, and a further layer directly on the first layer, the coating material of the first layer being wholly metal material, the further layer comprising at least 50 wt. % of zirconia, wherein the first layer is electrically conductive and may be connected to earth to provide electromagnetic shielding, and wherein the article is provided by a method in which the first layer is applied to the surface with only micro-scale melting of the surface by thermally spraying at a rate of less than 70 g/min, and in which the further layer is bonded to the first layer with only micro-scale melting of the surface by thermally spraying particles of size 50 to 90 micrometres at a rate of less than 100 g/min.

9. An article according to claim 1, wherein, the further layer comprises wholly or principally zirconia.

10. An article as claimed in claim 1, wherein the further layer is at least as thick as the first layer.

11. An article as claimed in claim 1, wherein the further layer is thicker than the first layer.

12. An article as claimed in claim 1, wherein the further layer is at least 100 micrometres thick.

13. An article as claimed in claim 1, wherein the further layer is at least 150 micrometres thick.

14. An article as claimed in claim 1, wherein the further layer is not greater than 300 micrometres thick.

15. An article as claimed in claim 8, wherein the further layer is not greater than 250 micrometres thick.

16. A method of coating a surface being made of a composite material including a matrix made of plastics material or a surface being made of an organic material, the method comprising thermal spraying a first layer of coating material directly onto the surface and to a thickness of less than 200 micrometres, and thus bonding the first layer of coating material to the surface with only micro-scale melting of the surface by thermally spraying at a rate of less than 70 g/min, and subsequently depositing a further layer directly on the first layer, the further layer being bonded to the first layer with only micro-scale melting of the surface by thermally spraying particles of size 50 to 90 micrometres at a rate of less than 100 g/min, the coating material of the first layer being wholly metal material, the further layer being of a material with a higher melting point than the coating material of the first layer, wherein the first layer is electrically conductive and may be connected to earth to provide electromagnetic shielding.

17. A method according to claim 16, wherein the first layer of coating material is plasma sprayed onto the surface.

18. A method according to claim 16, wherein the first layer up to 150 micrometres in thickness.

19. A method according to claim 16, wherein the first layer is up to 100 micrometres in thickness.

20. A method according to claim 16, wherein the further layer is deposited by plasma spraying.

21. A method according to claim 16, wherein the further layer is wholly or principally made of ceramic or metal or ceramic and metal.

22. A method according to claim 16, wherein the further layer is wholly or principally made of ceramic.

23. A method according to claim 21, wherein the further layer comprises at least 50 wt. % of zirconia.

24. A method as claimed in claim 23, wherein the further layer comprises wholly or principally zirconia.

25. A method according to claim 16, wherein the further layer is deposited to be at least as thick as the first layer.

26. A method according to claim 16, wherein the further layer is deposited to be thicker than the first layer.

27. A method according to claim 16, wherein the further layer is deposited to be at least 100 micrometres thick.

28. A method according to claim 16, wherein the further layer is deposited to be at least 150 micrometres thick.

29. A method according to claim 16, wherein the further layer is deposited to be not greater than 300 micrometres thick.

30. A method according to claim 16, wherein the further layer is deposited to be not greater than 250 micrometres thick.

31. An article according to claim 1, wherein the article is non-cylindrical.

32. An article according to claim 1, wherein the first layer is wider than the further layer.

33. An article according to claim 8, wherein the article is non-cylindrical.

34. An article according to claim 8, wherein the first layer is connected to an earth surface to provide electromagnetic shielding.

35. An article according to claim 8, wherein the first layer is wider than the further layer.

36. A method according to claim 16, wherein the article is non-cylindrical.

37. A method according to claim 16, wherein the surface is mounted on a coupon for spraying, and the coupon is static during spraying of the first layer and further layer.

38. A method according to claim 16, wherein the first layer is wider than the further layer.

39. An article according to claim 1, wherein the article has a complex geometry.

40. An article according to claim 8, wherein the article has a complex geometry.

41. An article according to claim 16, wherein the article has a complex geometry.

42. A method according to claim 16, wherein the surface is mounted on a rotating turntable for spraying.

43. A method according to claim 16, wherein the first layer of coating material is thermal sprayed by hand spraying.

44. A method according to claim 43, wherein the surface is of a complex shape.

45. A method according to claim 16, wherein the further layer is thermal sprayed by hand spraying.

46. A method according to claim 45, wherein the surface is of a complex shape.

47. An article according to claim 8, wherein the further layer is a thermal barrier layer.

48. An article according to claim 1, wherein the further layer is a thermal barrier layer.

49. An automobile part comprising a surface coated according to the method of claim 16.

\* \* \* \* \*